United States Patent [19]

Lee

[11] Patent Number: 5,066,580
[45] Date of Patent: Nov. 19, 1991

[54] XANTHENE DYES THAT EMIT TO THE RED OF FLUORESCEIN

[75] Inventor: Linda Lee, Mountain View, Calif.

[73] Assignee: Becton Dickinson and Company, N.J.

[21] Appl. No.: 481,010

[22] Filed: Feb. 16, 1990

Related U.S. Application Data

[62] Division of Ser. No. 233,945, Aug. 31, 1988, Pat. No. 4,933,471.

[51] Int. Cl.$^5$ .................. C12Q 1/00; C12Q 1/44; C12Q 1/02; G01N 33/53; G01N 33/48; G01N 1/30; G01N 31/00
[52] U.S. Cl. .................. 435/721; 435/724; 435/7.5; 435/19; 435/29; 435/960; 435/968; 436/800; 436/805; 436/63; 424/3
[58] Field of Search ............ 435/7, 29, 34; 436/172, 436/800, 805, 7.24, 7.5, 19, 63; 424/3

[56] References Cited

U.S. PATENT DOCUMENTS 4,599,307 7/1986 Saunders et al. ............... 435/34
4,727,020 2/1988 Recktenwald ................... 435/6

OTHER PUBLICATIONS

Orndorff et al., *J. Am. Chem. Soc.*, 46:1986, 1924.
Herzenberg et al., *Sci. Am.*, 234:10, 1976.
Rink et al., *J. Cell. Biol.*, 95-189, 1982.

*Primary Examiner*—Esther L. Kepplinger
*Assistant Examiner*—Jacintha M. Stall
*Attorney, Agent, or Firm*—Brian K. Stierwalt; Robert M. Hallenbeck

[57] ABSTRACT

Novel xanthene dyes are disclosed which excite in the range of 450–650 nm and which will emit to the red of fluoroscein. These dyes may be coupled to tagging agents, such as monoclonal antibodies, and used to detect cells in a sample.

21 Claims, 8 Drawing Sheets

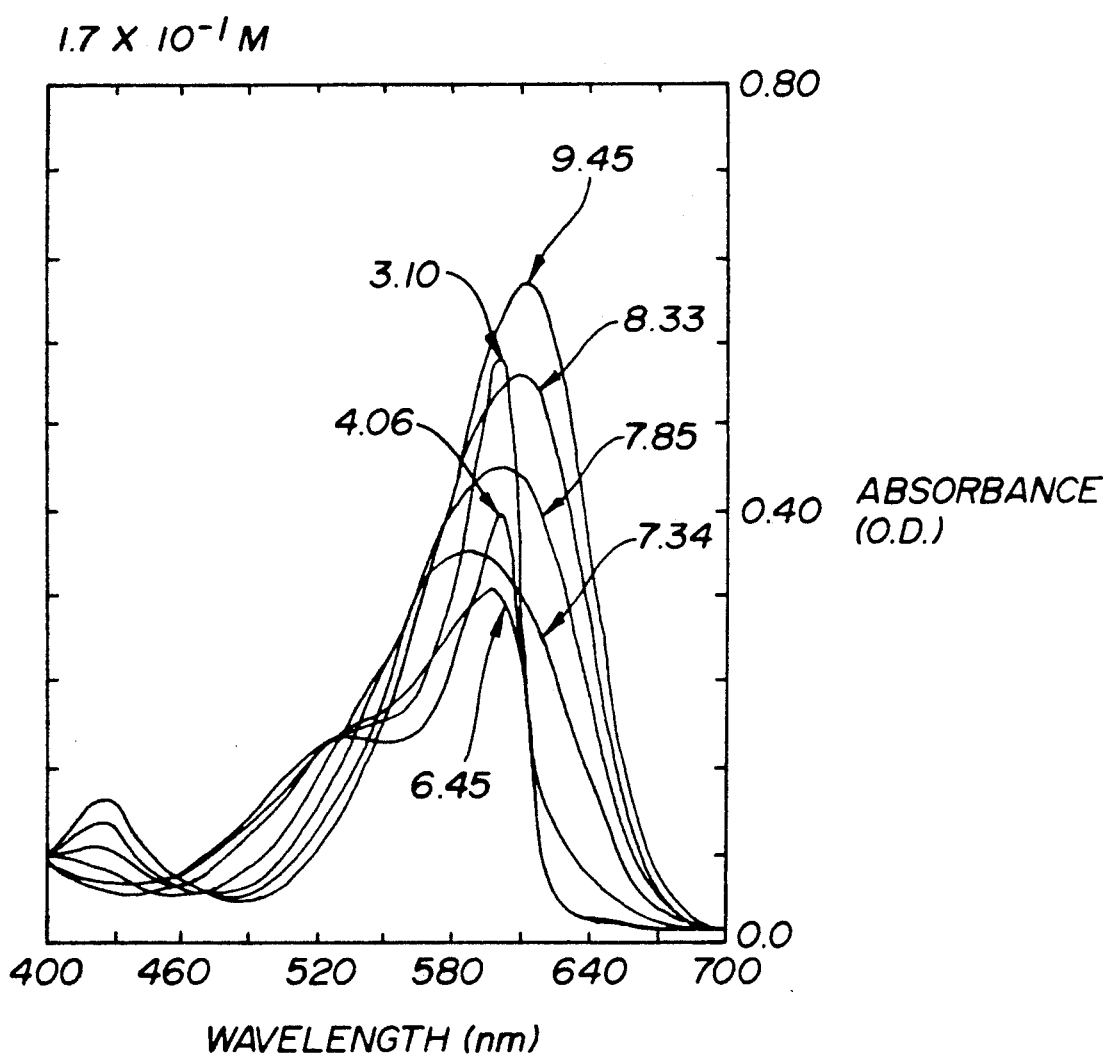

XANTHENE DYES THAT EMIT TO THE RED OF FLUORESCEIN

This is a division, of application Ser. No. 238,945, filed Aug. 31, 1988, now U.S. Pat. No. 4,933,471.

FIELD OF THE INVENTION

This invention relates to novel xanthene dyes, and more particularly, this invention relates to fluorescent sulfonexanthene dyes that may be used in cell analysis.

BACKGROUND OF THE INVENTION

Xanthene dyes are among the most commonly used class of fluorescent dyes. Fluorescein, a dihydroxy xanthene dye, is a particularly useful biological dye for several reasons: the dianionic form of the dye is very soluble in water; its $pK_a$ is 6.3 6.7 thus being mostly deprotonated and fluorescent at physiological pH (7.0–7.6); the excitation maxima of the dye (490 nm) is well matched to a 488 nm line of an argon ion laser; it has a high extinction coefficient ($8 \times 10^4 M^{-1} cm^{-1}$); and a high quantum yield (0.93). The last two properties allow the detection of minute quantities of the dye.

In addition to these properties, derivatives of fluorescein are readily synthesized, and allow utilization of the dye for biological purposes (e.g., fluorescein diacetate has utility as a membrane permeable esterase substrate). One derivative, fluorescein isothiocyanate (FITC), has been used extensively in the field of flow cytometry.

Flow cytometers generally are characterized as having one or more sources of excitation (typically lasers tuned to a specific frequency), means which allow the passage of cells substantially one at a time through a measurement region and means for detection of light scatter and fluorescence from cells as they pass through the measurement region. Means to record the data for each of the cells also may be coupled to the device.

Fluorescein isothiocyanate typically is used in such systems coupled to a monoclonal antibody (MAb) which will react with certain cells in a sample, although it may be coupled to any type antibody. When cells bearing the MAb conjugated to FITC pass through the measurement region, the laser excites the dye and fluorescence is emitted and collected by one of the detection means. An article by Herzenberg et al., Sci. Amer., (1979) and U.S. Pat. No. 4,599,307 describe a typical flow cytometer and describe the use of FITC conjugated MAbs to detect the presence of certain cells. U.S. Pat. No. 4,727,020 further describes a method for the analysis of subpopulations of blood cells using FITC conjugated MAbs in combination with other tagging agents, such as a nucleic acid dye.

The usefulness of fluorescein isothiocyanate, however, is somewhat limited in that it is excited at 488 nm and emits at 520 nm. It would be useful to have the characteristics of FITC but with an excitation maxima to the red of fluorescein. The advantages of a dye with a longer wavelength excitation and emission are several: background fluorescence from biological materials (e.g., DNA) diminishes; the cost and size of the laser needed to excite the dye diminishes; and the possibility of dual laser excitation using an argon ion laser as the lower wavelength laser rises. As such, dyes having such properties would be useful in the analysis of cells in a sample.

SUMMARY OF THE INVENTION

This invention provides for novel xanthene dyes which have excitation and emission maxima to the red of fluorescein. Xanthene dyes of this invention comprise derivatives of sulfonefluorescein and naphthosulfone fluorescein as well as derivatives of fluorescein and naphthofluorescein. Derivatives of sulfonefluorescein and naphthosulfonefluorescein are preferred, and in particular, a naphthosulfonefluorescein named Vita Blue is especially preferred.

Xanthene dyes described in this invention are useful in cell analysis. A sample of cells may be taken from a variety of solid tissues (e.g., spleen and thymus) and body fluid (e.g., blood, urine and bone marrow), and may be analyzed when combined with tagging agents (e.g., monoclonal antibodies) which are reactive with specific cell types. These tagging agents may be coupled directly to the novel dyes of this invention or indirectly by means well known in the art such as biotin-avidin complexes. Additionally other forms of the dyes described in this invention may be used as an intracellular pH indicators and as means to discriminate between "live" and "dead" cells.

Analyses of cells in the sample may be done using any means capable of detecting fluorescence from the labelled cells. A fluorescent light microscope is one such means, and a flow cytometer (such as FACScan ™ or FACStar ™, Becton Dickinson Immunocytometry Systems (BDIS)) may be used as automated means.

DETAILED DESCRIPTION OF THE INVENTION

Figure 1:
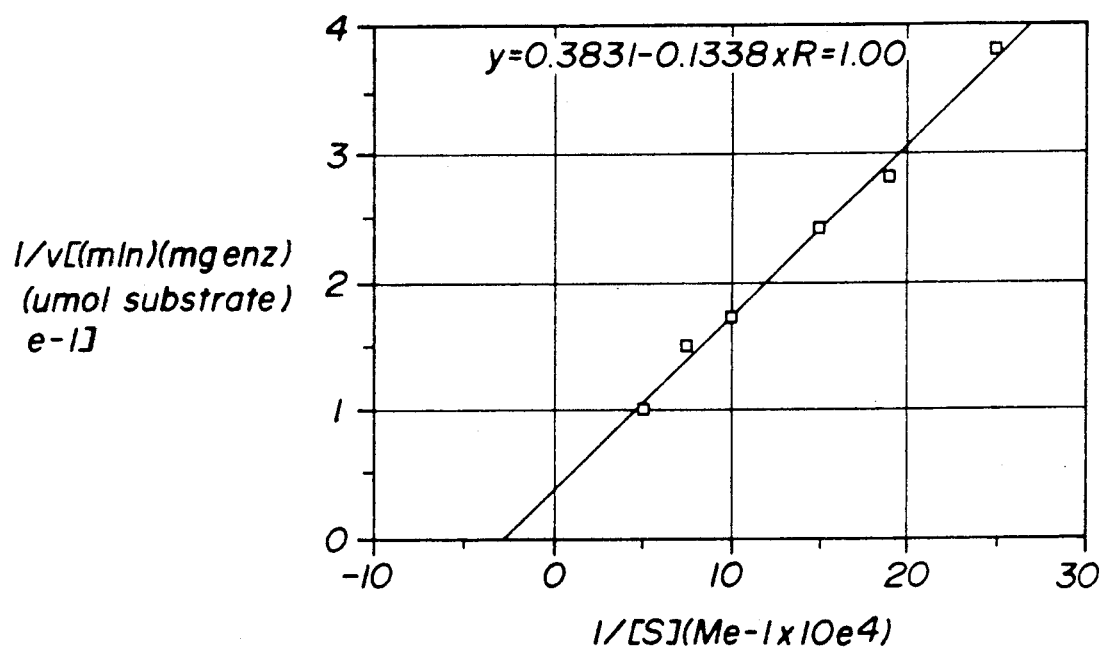
FIG. 1 is a Lineweaver-Burk plot of VBDB (compound 14) with pig liver esterase.
Figure 2A:
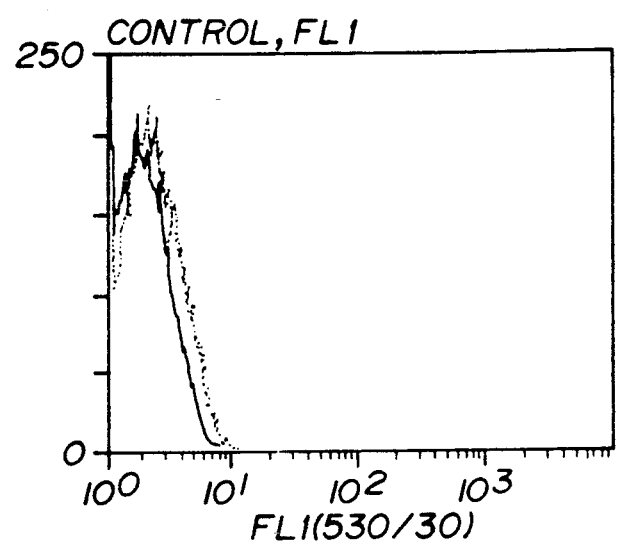
FIG. 2 comprises several histograms of log fluorescence for human white blood cells-stained with BCECF, or VBDB wherein (a) and (d) represent unstained cells using a 530/30 bandpass filter and 660/20 bandpass filter respectively, (b) represents cells stained with BCECF using a 530/30 bandpass, (c) represents cells stained with FDA using a 530/30 bandpass, and (e) and (f) represent cells stained with VBDB using a 660/20 bandpass.
Figure 2B:
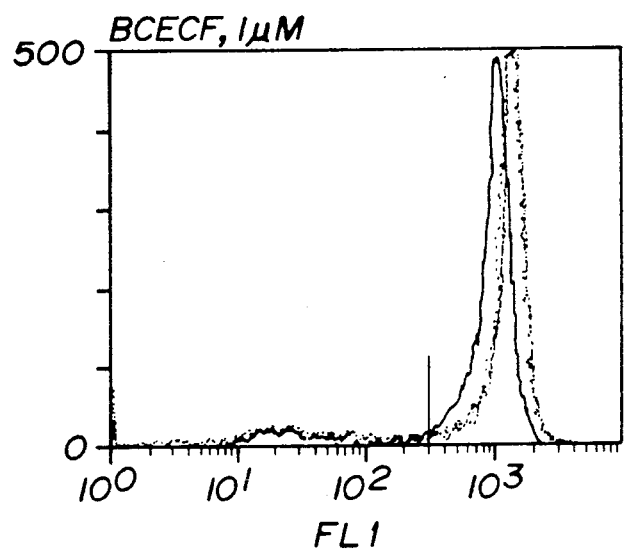
Figure 2C:
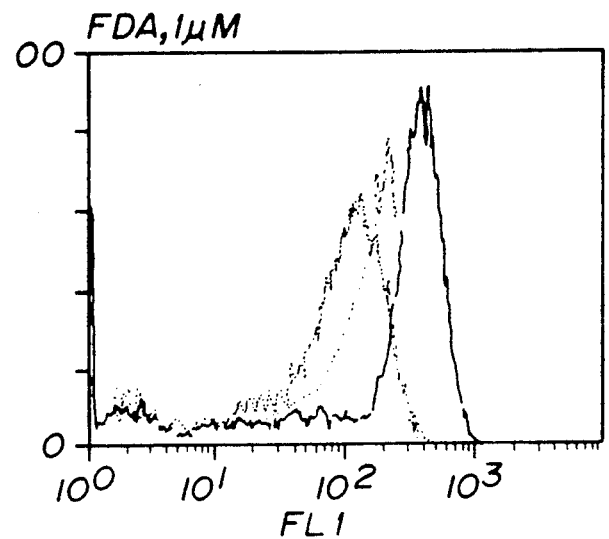
Figure 2D:
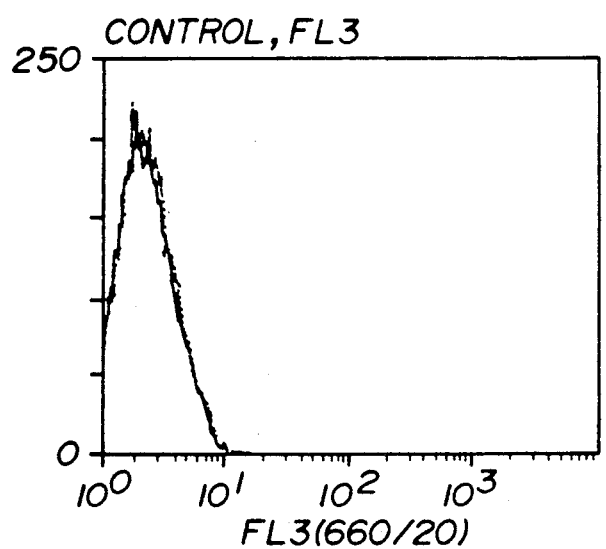
Figure 2E:
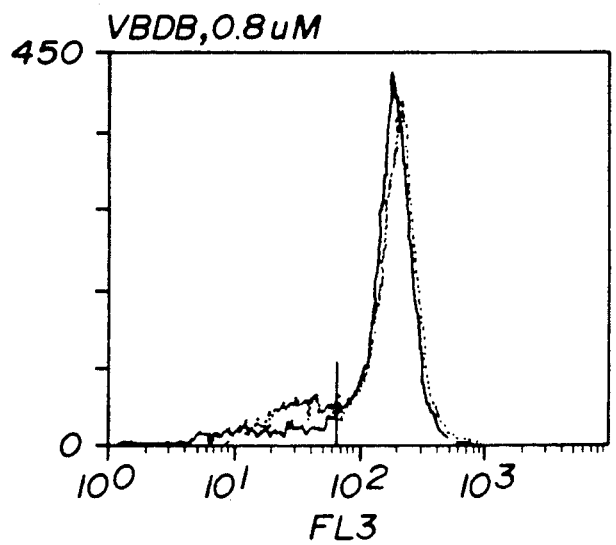
Figure 2F:
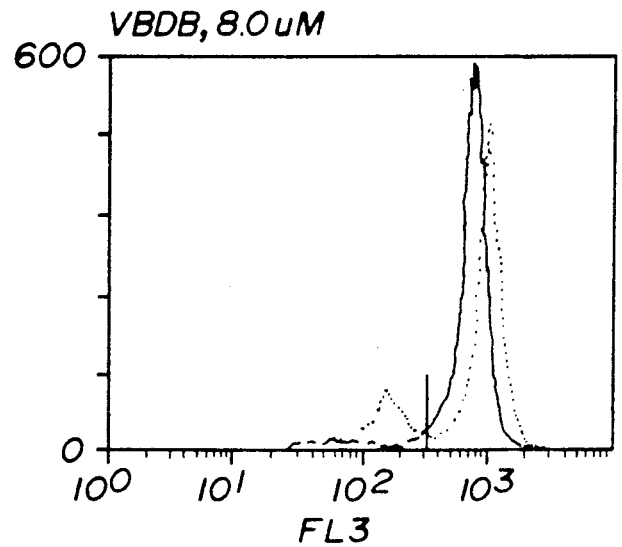

The xanthene compounds which form the basis of this invention were prepared by the following methods. Unless otherwise indicated, all chemicals were obtained from Aldrich Chemical Co. The basic structure for xanthene dyes is given below:

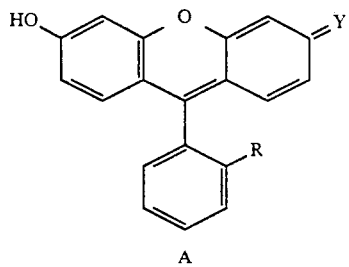

A

1  R = CO₂H, Y = O
2  R = SO₃H, Y = O
3  R = CO₂H, Y = +N(CH₃)₂

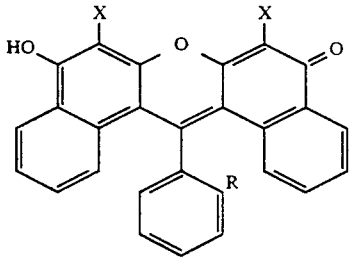

B

4  R = CO₂H, X = H
5  R = CO₂H, X = Br
6  R = SO₃H, X = H

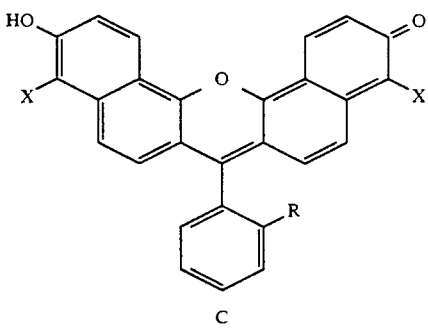

C

7  R = CO₂H, X = H
8  R = CO₂H, X = Br
9  R = SO₃H, X = H

The structure of fluorescein is shown as compound 1. Sulfonefluorescein, compound 2, was made as follows: Resorcinol (2 g, 18 mmol), 2-sulfobenzoic anhydride (1.7 g, 9 mmol), polyphosphoric acid (8 g) were combined in a round bottomed flask and heated in an oil bath for 3.5 h. The resulting red solution was poured into water and the solid filtered. The solid was dissolved in 10% NaHCO₃ solution and filtered. The filtrate was heated to boiling and acidified with concentrated HCl. The solid was filtered and dried. Yield: 1.85 g (55%). ¹H NMR (DMSO-d₆): δ8.0 (d, K=8 Hz, 1 H), 7.69 (m, 1 H), 7.60 (m, 1 H), 7.4 (d, J =10 Hz, 2 H), 7.28 (m, 3 H), 7.16 (m, 2 H).

Sulfonefluorescein diacetate, compound 13, was prepared as follows. Sulfonefluorescein (0.28 g, 0.76 mmol) was refluxed with acetic anhydride (15 mL) for 7 h. The solution then was cooled overnight. The next day dark green shiny crystals were filtered and dried to constant weight. Yield: 0.2 g (64%). ¹H NMR of the solid indicated it was a mixture of the mono- and diacetates. The diacetate could be purified by medium pressure chromatography on silica gel. A solution of the mono- and diacetates (20 mg) in CH₂Cl₂(0.5 mL) was loaded onto silica gel and rapidly eluted with additional CH₂Cl₂. The monoacetate appeared to be hydrolyzed under these conditions, and a layer of red solid (presumably compound 2) remained at the top of the column. The filtrate was concentrated to a yellow solid (5 mg). ¹H NMR (CDCl₃): δ8.12 (d, J=8 Hz, 1 H), 7.71 (m, 1 H), 7.62 (m, 1 H), 7.49 (d, J=9 Hz, 2 H), 7.46 (d, J=2 Hz, 2 H), 7.10 (dd, J=9 Hz, 2 Hz, 2 H), 7.05 (d, J=8 Hz, 1 H), 2.35 (s, 6 H).

Rhodol, compound 3, was prepared as follows. Fluorescein (3.2 g, 9.6 mmol), sodium hydroxide (6.4 g, 0.17 mmol) and water (3.2 mL) were heated with stirring in an oil bath for 3 h. The solution turned purple, then yellow. The solution was cooled, water (20 mL) was added, and the solution acidified to pH 1 with concentrated HCl. The resulting mixture (a yellow oil plus a white solid) was extracted with ether and the ethereal portion concentrated. The oil was recrystallized from an ethanol-water mixture, providing yellow shiny needles (1.5 g, 60%). Mp: 210° C.

A mixture of 2-carboxy-2',4'-dihydroxybenzophenone (0.87 g, 2.8 mmol), 3-dimethylaminophenol (0.39 g, 2.8 mmol) and zinc chloride (0.38 2.8 mmol) then were combined in a round bottomed flask and heated in an oil bath overnight. Thin layer chromatography (silica gel, ethyl acetate) of a small portion of the reaction mixture dissolved in ethanol showed a mixture of fluorescein, rhodamine and rhodol. The mixture was purified by medium pressure chromatography on silica gel using ethyl acetate followed by a 1:1 mixture of ethyl acetate and ethanol. Fractions containing rhodol and rhodamine were concentrated, triturated with a mixture of 1:10 methanol and ethyl acetate, filtered and dried. Yield: 0.2 (21%) red solid. ¹H NMR (DMSO d6) δ8.03 (d, J=7 Hz, 1 H), 7.66 (m, 2 H), 7.2 (d, J=7 Hz, 1 H), 6.62–6.40 (m, 6 H), 2.98 (s, 6 H).

The basic structure of the compounds shown in A then was modified to form the compounds set forth in B. In particular, 1,2,7,8 dibenzofluorescein compound 4, was prepared as follows. In a round bottomed flask, 1,3-dihydroxynaphthalene (1 g, 6.3 mmol) and phthaloyl dichloride (0.63 g, 3.1 mmol) were heated briefly in an oil bath. Water (30 mL) and sodium hydroxide (1 g) were added. The solution was acidified with concentrated HCl and filtered. The solid was refluxed with acetic anhydride (30 mL) until homogeneous. The solution was cooled overnight. The diacetate was filtered and collected as a pale orange solid. ¹H NMR (CDCl₃): δ8.19 (d, J=8 Hz, 1 H), 7.92 (m, 2 H), 7.55 (m, 4 H), 7.3 (m, 6 H), 7.21 (d, J=7 Hz, 1 H), 2.50 (s, 6 H). Sodium hydroxide (1 g) and ethanol (10 mL) were added to the diacetate in a round-bottomed flask and the mixture was concentrated to dryness under reduced pressure. Water (20 mL) and concentrated HCl were added; the solid was filtered and dried. Yield: 0.34 g (24%).

1,2,7,8-Dibenzo-4,5-dibromofluorescein compound 5, was prepared as follows. 1,2,7,8 Dibenzofluorescein (0.25 g, 0.58 mmol), bromine (0.4 g, 2.3 mmol) and acetic acid (3 mL) were combined in a round bottomed flask equipped with a magnetic stirring bar and a reflux condenser. The mixture was refluxed for 1 h. Water (20 mL) was added, the mixture was filtered, and the red solid dried. Yield: 0.21 g (62%). This compound was purified by conversion to the diacetate and hydrolysis in basic ethanol as described for compound 4. ¹H NMR of the diacetate (CDCl₃) δ8.15 (d, J=7 Hz, 1 H), 7.83 (m, 2 H), 7.65 (d, J=8 Hz, 2 H), 7.55 (m, 2 H), 7.36 (m, 4 H), 7.26 (d, J=7 Hz, 1 H), 2.54 (s, 6 H).

1,2,7,8-Dibenzosulfonefluorescein compound 6, was prepared as follows. In a round bottomed flask, 1,3-dihydroxynaphthalene (2 g, 12.5 mmol) and 2-chlorosulfonylbenzoyl chloride, compound 10 (1.5 g, 6.3 mmol), were combined and heated briefly in an oil bath. The dark solid was dissolved in hot, 10% NaHCO$_3$ solution and filtered. The dark residue (0.2 g) was discarded. The filtrate was heated to boiling and acidified with concentrated HCl. The solid was filtered and refluxed with hot ethanol (150 mL). The solid was filtered and dried. Yield: 0.9 g (30%) red solid. $^1$H NMR (DMSO-d$_6$, 60° C.): δ8.31 (d, J 8 Hz, 2 H), 8.13 (d, J=8 Hz, 1 H), 7.81 (m, 1 H), 7.63 (m, 1 H), 7.48 (m, 2 H), 7.24 (d, J=8 Hz, 1 H), 7.16 (m, 2 H), 7.02 (s,2 H), 6.96 (d, J=9 Hz, 2 H).

The general formula for xanthene dyes set forth in A further was modified to form the compounds set forth in C. In particular, naphthofluorescein, compound 7, was prepared as follows. In a round bottomed flask, 1,6-dihydroxynaphthalene (10 g, 63 mmol), phthalic anhydride (4.6 g, 31 mmol) and zinc chloride (4.2 g) were combined and heated in an oil bath for 2 h. Sodium hydroxide (15 g) and water (100 mL) were added to the reaction mixture. The blue solution was filtered through CELITE (diatomaceous earth), acidified with concentrated HCl and filtered. The solid was dried. Yield: 12.5 (93%). The crude dye was purified by conversion to the diacetate (41% yield) followed by hydrolysis in basic ethanol (85% yield) as described for compound 4. $^1$H NMR of the diacetate (CDCl$_3$): δ8.76 (d, J 9 Hz, 2 H), 8.11 (m, 1 H), 7.64 (m, 2 H), 7.59 (d, J=2 Hz, 2 H), 7.48 (m, 4 H), 7.08 (m, 1 H), 6.87 (d, J 9 Hz, 2 H), 2.34 (s, 6 H). $^1$H NMR of compound 7 (DMSO-d$_6$): δ8.67 (d, J =9 Hz, 2 H), 8.08 (m, 1 H), 7.75 (m, 2 H), 7.44 (d, J =9 Hz, 2 H), 7.36 (dd, J=9 Hz, 2 H), 7.29 (m, 1 H), 7.20 (d, J=2 Hz, 2 H), 6.68 (d, J=9 Hz, 2 H).

4,10 Dibromonaphthofluorescein compound 8, was prepared as follows. In a round bottomed flask equipped with a magnetic stirring bar and reflux condenser, naphthofluorescein (0.25 g, 0.58 mmol), bromine (0.56 g, 3.5 mmol) and acetic acid (2 mL) were combined and refluxed for 1 h. The bromine and acetic acid were removed by distillation. Acetic anhydride (5 mL) was added and the mixture refluxed until the mixture was colorless. The mixture was cooled and filtered. Yield: 0.32 (78%) white solid. $^1$H NMR of diacetate (CDCl$_3$): δ8.74 (d, J 9 Hz, 2 H), 8.13 (m, 1 H), 7.95 (d, J=9 Hz, 2 H), 7.66 (m, 2 H), 7.50 (d, J=9 Hz, 2 H), 7.04 (m, 1 H), 6.99 (d, J=9 Hz, 2 H), 2.46 (S, 6H). The diacetate was hydrolyzed in basic ethanol as described for compound 4(98% yield).

2-Chlorosulfonylbenzoylchloride, compound 10, was prepared as follows during the synthesis of Vita Blue (compound 9). 2-Sulfobenzoic anhydride .(25 g, 0.13 mol) and phosphorus pentachloride (56 g, 0.27 mol) were combined in a round bottomed flask equipped with a magnetic stirring bar and reflux condenser. The mixture was heated with stirring in an oil bath for 2 h, poured onto ice and extracted with ether. .The ethereal solution was extracted with dilute ammonium hydroxide solution until the extracts were basic (pH 10). This step converts the "unsymmetric" dichloride, compound 11, into the cyano derivative, compound 12. The ethereal solution was dried and concentrated to a white solid (Mp:75°-78° C., lit: 79° C.). Yield: 8.1 g (26%).

Vita Blue, compound 9, was prepared as follows and in accordance with the schematic below. In a round bottomed flask 2-chlorosulfonylbenzoyl chloride (3.5 g, 15 mmol), 1,6-dihydroxynaphthalene (4.7 g, 29 mmol) and zinc chloride (2 g, 15 mmol) were combined and heated in an oil bath. Reactions conducted without any catalyst gave yields which were comparable to reactions with zinc chloride.

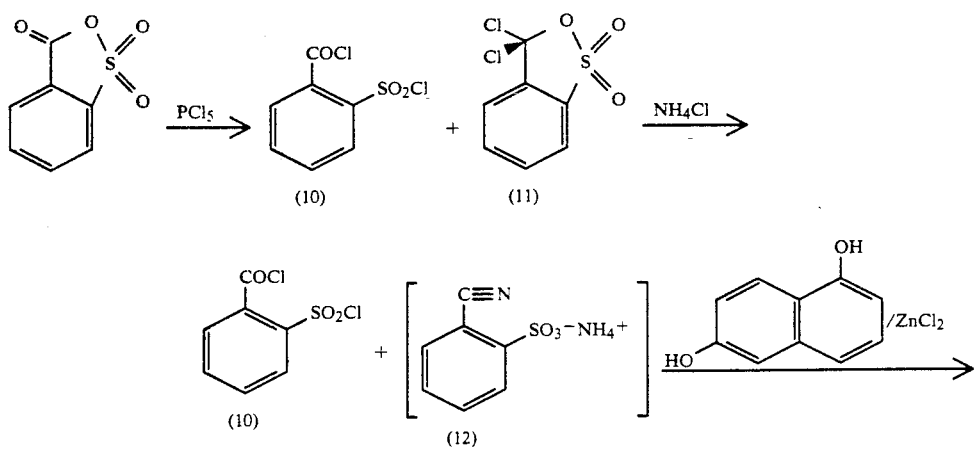

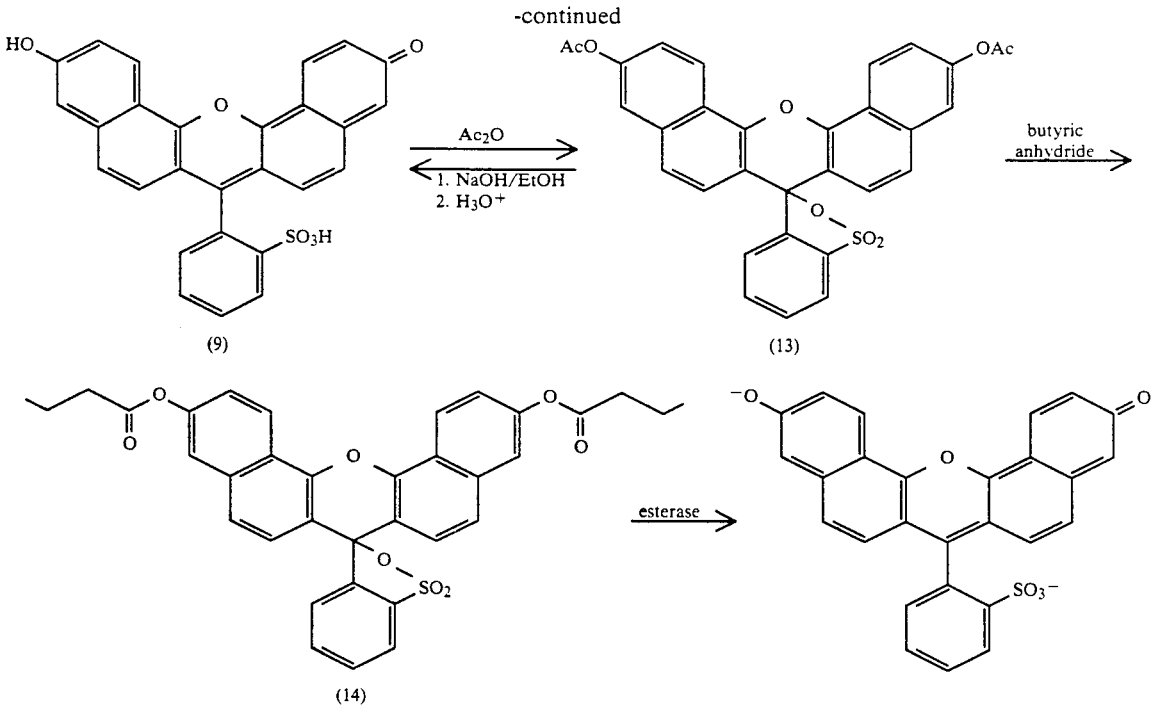

After 1 h, the mixture had turned into a black solid. Sodium hydroxide (6 g, 0.15 mol) and water (100 mL) were added. The dark solution was filtered. The filtrate was acidified with concentrated HCl and filtered. The dark solid was transferred to an Erlenmeyer flask equipped with a magnetic stirring bar. Ethanol (150 mL) was added, the mixture was brought to a boil with stirring and allowed to cool overnight. The next day the mixture was filtered. A purple solid consisting of crude dye, compound 9, was obtained. Yield: 0:15 g (2%). The dye was purified by conversion to the diacetate, compound 13, followed by hydrolysis.

Modifications to Vita Blue then were made as follows. Vita Blue diacetate, compound 13, was prepared as follows. In a round bottomed flask, crude Vita Blue (15 g, 0.32 mmol) was reflexed with acetic anydride (100 mL) until the solution appeared to be homogeneous. The solution was filtered while hot under reduced pressure through a Buchner funnel. The filtrate was concentrated to half the original volume by distilling the acetic anhydride at atmospheric pressure. A red-orange solid appeared, and the solution was allowed to cool overnight. The next day the mixture was filtered and a red-orange solid was obtained (23 mg). The filtrate was concentrated and the dark brown solid which appeared was filtered. The dark brown solid was recrystallized from 4 mL acetic anhydride, providing additional red-orange solid (17 mg). Total yield: 40 mg (22%). The solid did not melt, but decomposed above 250° C. $^1$H NMR (CDCl$_3$): δ8.9 (d, J=9 Hz, 2 H), 8.62 (d, J=8 Hz, 1 H), 7.84 (m, 1 H), 7.50 (d, J=9 Hz, 2 H), 7.61 (m, 3 H), 7.48 (m, 4 H), 7.03 (d, J=8 Hz, 1 H), 2.39 (s, 6 H).

Vita Blue dibutyrate (VBDB, compound 14), was prepared as follows. In a round bottomed flask, Vita Blue diacetate (13 mg, 0.023 mmol) was reflexed with butyric anhydride (5 mL) until the solution was homogeneous. The solvent was removed by distillation under reduced pressure provided by a water aspirator. Additional butyric anhydride (5 mL) was added and the solution refluxed briefly. The solvent was removed under reduced pressure until about 0.5 mL was remaining. The resulting bright orange solid was filtered, washed with ether, and dried (1 mmHg). Yield: 13 mg (93%). The solid did not melt but decomposed above 250° C. $^1$H NMR (CDCl$_3$): δ8.83 (d, J=9 Hz, 2 H), 8.63 (d, J=8 Hz, 1 H), 7.83 (m, 1 H), 7.66 (d, J=9 Hz, 2 H), 7.6 (m, 3 H), 7.45 (m, 4 H), 7.03 (d, J=8 Hz, 1 H), 2.62 (t, J=7 Hz, 4 H), 1.84 (m, 4 H), 1.10 (t, J=7 Hz, 6 H).

Vita Blue also can be prepared from Vita Blue diacetate by the following method. Ethanol (5 mL) was warmed with solid sodium hydroxide (0.2 g, 5 mmol) in a round bottomed flask until the solid was mostly dissolved. Vita Blue diacetate (18 mg, 0.033 mmol) was added. The solution immediately turned blue-green. The solution was concentrated to dryness on a rotary evaporator. Water (20 mL) and concentrated HCl (1 mL) were added. The mixture was filtered and the resulting purple solid was dried in an oven. Yield: 15 mg (97%). $^1$H NMR (DMSO-d$_6$): δ11.52 (br s, 1 H), 9.26 (d, J=9 Hz, 2 H), 8.07 (d, J=8 Hz, 1 H), 7.92 (d, J=9 Hz, 2 H), 7.76 (m, 1 H), 7.67 (m, 1 H), 7.67 (m, 1 H), 7.52 (dd, J=9 Hz, 2 Hz, 2 H), 7.45 (d, J=2 Hz, 2 H), 7.31 (d, J=8 Hz, 1 H), 7.25 (d, J=9 Hz, 2 H).

Compounds 3, 6, 9 and the derivatives of 9 comprise the derivatives of sulfonefluorescein and naphthosulfonefluorescein of this invention. The remaining compounds comprise the derivatives of fluorescein and naphthofluorescein of this invention. Following their preparation, each compound was analyzed for its fluorescence properties which are summarized in Table I.

TABLE I

| Cmpd | Abs Max (nm) | $\epsilon$ (M$^{-1}$cm$^{-1}$) | EM Max (nm) | Quantum Yield | pK$_{a3}$ |
|---|---|---|---|---|---|
| 1 | 491 | 8.0 × 10$^4$ | 516 | 0.92 | 6.33 +/− 0.04 |
| 2 | 497 | 7.8 × 10$^4$ | 517 | 0.92 | 6.23 +/− 0.04 |
| 3 | 522 | 5.7 × 10$^4$ | 545 | 0.20 | 5.50 +/− 0.04 |
| 4 | 534 | 8.1 × 10$^4$ | 565 | 0.24 | 6.02 +/− 0.04 |
| 5 | 549 | 2.4 × 10$^4$ | 581 | 0.05 | 3.92 +/− 0.03 |

TABLE I-continued

| Cmpd | Abs Max (nm) | $\epsilon$ (M$^{-1}$cm$^{-1}$) | EM Max (nm) | Quantum Yield | $pK_{a3}$ |
|---|---|---|---|---|---|
| 6 | 541 | $8.1 \times 10^4$ | 567 | 0.48 | 5.95 +/− 0.05 |
| 7 | 595 | $4.4 \times 10^4$ | 660 | 0.14 | 7.99 +/− 0.02 |
| 8 | 605 | $3.2 \times 10^4$ | 682 | 0.05 | 7.45 +/− 0.04 |
| 9 | 609 (pH 9.5) | $3.6 \times 10^4$ | 665 | 0.15 | 7.56 +/− 0.03 |
| 9 | 524 (pH 5.2) | $1.3 \times 10^4$ | 570 | 0.04 | ND |
| 14 | 480 | $5.9 \times 10^3$ | 552 | 0.03 | ND |

First, the extinction coefficient of compounds 1-9 and 14 was determined. Stock solutions ($5 \times 10^{-3}$ M) of each dye were made by dissolving the dye in two equivalents of 0.1 N NaOH and making up the volume with carbonate/bicarbonate buffer (0.16, 0.34 M, pH 9.5). The solution was diluted ($2 \times 10^{-5}$ M) in additional buffer (final pH 9.5-10) and the absorbance spectrum measured. A stock solution ($1.2 \times 10^{-3}$ M) of Vita Blue was prepared in DMSO, diluted into citrate buffer (0.1 M, pH 5 2) to give a final concentration of $1.6 \times 10^{-5}$ M and the absorbance spectrum measured. A stock solution ($8.2 \times 10^{-3}$ M) of VBDB was prepared in DMSO and diluted into pyrophosphate buffer (0.1 M, pH 7.2) to give a final concentration of $8.1 \times 10^{-5}$ M and the absorbance spectrum measured on a Beckman model DU-6UV visible spectrophotometer.

Second, quantum yields of compounds 1-9 and 14 were measured. Solutions ($1 \times 10^{-6}$ M) of compounds 1-9 were prepared in carbonate/ bicarbonate buffer (pH 9.5). Fluorescence emission spectra were measured on a Perkin-Elmer MPF-2A fluorescence spectrophotometer in 3-mL disposable plastic cuvettes. The excitation wavelength was set 30 nm to the red of the maximum excitation wavelength and the emission spectra measured. The area under the emission spectrum was measured (F). The quantum yield ($\Phi$) was determined using the following equation, $F = kI_o\Phi\epsilon cb$, where F is the fluorescence, k is a fluorimeter constant, $I_o$ is the light intensity at the exciting wavelength, $\epsilon$ is the extinction coefficient at the exciting wavelength, c is the concentration of the dye, and b is the pathlength of the cuvette. The value of k was determined for three different emission wavelength regions by using literature values of $\Phi$ and measuring the fluorescence of fluorescein (470-670 nm, $\Phi=0.92$), eosin (500-700 nm, $\Phi=0.19$) and allophycocyanin (Applied BioSystems, 600-800 nm, $\Phi=0.68$). The value of $I_o$ was determined from a table that was generated by scanning the range of exciting wavelengths on the fluorescence spectrophotometer with the emission monochrometer open; a piece of white paper was placed in the sample holder to reflect the exciting light. The concentration of the dyes were 0.6-1.0 uM; this value in each case was below the concentration ($0.005/\epsilon$) required in order for the equation to be valid.

Fluorescence titration of compounds 1-9 also was performed. Compounds 1-9 were titrated in 3 mL quartz cuvettes. The following procedure describes the titration for Vita Blue. To a cuvette the following solutions were added: Vita Blue (75 uL, $3.3 \times 10^{-5}$ M), EPPS buffer (0.2 mL, 0.1 M, pH 8.6), pyrophosphate buffer (0.2 mL, 0.1 M, pH 10) and water (2.52 mL). The final concentration of the dye was $8.2 \times 10^{-7}$ M. The pH and the fluorescence (excitation wavelength=620 nm, emission wavelength×660 nm) of the solution was measured. Concentrated HCl (1 uL, 1.0 N) was added and the pH and the fluorescence measured again. This procedure was repeated until the final fluorescence was 10% of the initial fluorescence.

Absorbance titration of Vita Blue then was measured. To a plastic cuvette (3 mL) was added the following solutions: citrate buffer (0.1 mL, 0.1 M, pH 4.2), pyrophosphate buffer (0.1 mL, 0.1 M, pH 6.2), EPPS buffer (0.1 mL, 0.1 M, pH 8.4), water (2.6 mL), HCl solution (5 uL, 6 N) and Vita Blue solution (8 or 40 uL, $1.25 \times 10$ M). The final concentration of Vita Blue was $3.4 \times 10^{-6}$ or $1.7 \times 10^{-5}$ M. The initial pH was approximately 3. Aliquots of NaOH solution were added (1-3 uL, 4 N) and the pH and the absorbance spectrum from 700 to 400 nm measured.

Fluorescence emission spectra of Vita Blue also was determined. To each of five plastic cuvettes (3 mL) were added one of the following buffered solutions (0.1 M): citrate buffer (pH 4.21), pyrophosphate buffer at three pH values (6.22, 7.21, 9.05), and EPPS buffer (pH 8.37). Vita Blue solution (5 uL, $1.25 \times 10^{-3}$ M) was added, and the fluorescence emission spectra from 450 to 650 nm was measured. The excitation wavelength was 540 nm.

Finally, a determination of $K_m$ of VBDB was made. VBDB (5 mg, $8.2 \times 10^{-3}$ mmol) was dissolved in DMSO (1 mL) to give a yellow solution ($8.2 \times 10^{-3}$ M). The solution (30 uL) was diluted in EPPS buffer (12 mL, 0.1 M, pH 8.0); the final concentration was $2.0 \times 10^{-5}$ M. This solution was diluted to a range of concentrations ($4.0 \times 10^{-6}$ M to $2 \times 10^{-5}$ M) with EPPS buffer (pH 8.0) and the change in O.D. at 608 nm measured after addition of esterase (Sigma Chemical, E.C. 3.1.1.1, 8 ug). A Lineweaver-Burk plot is shown in FIG. 1. The $K_m$ was found to be $4 \times 10^{-5}$ M; the specific activity was 2.5 (ug substrate) (min)$^{-1}$(mg enzyme)$^{-1}$.

After characterizing the various xanthene dyes prepared in accordance with this invention, one of the dyes (VBDB) was used to stain cells. The ability of VBDB to stain cells was compared with BCECF-AM, a membrane permeable esterase substrate (Molecular Probes) and fluorescein diacetate (FDA). To a centrifuge tube, human whole blood (1.5 ml) and ammonium chloride lysing solution (30 ml, 0.15 M NH4Cl, 10 mM KHCO3, 0.11 mM EDTA, pH 7.3) were added. After incubation, the tube was centrifuged. This procedure specifically lyses red blood cells leaving the white cells intact and viable. The supernatant was removed and the white blood cells which remained were washed twice and resuspended in blood cell diluent (1 mL, Diagnostic Technology, Inc.). The cell concentration and the percentage of dead cells were ascertained by counting the cells manually using a fluorescent microscope and a hemacytometer; acridine orange and ethidium bromide were used to stain live and dead cells respectively. The cell concentration was $2.8 \times 10^7$ cells/mL and the percentage of dead cells was 2-4%.

Four samples of approximately $1.7 \times 10^6$ cells then were placed in polystyrene tubes. To each tube was added one of the following solutions (1 mL): FDA (1 uM) BCECF-AM (1 uM), VBDB (0.8 uM), or VBDB (8.0 uM). The dye solutions were prepared by diluting a stock solution of each dye (1-8 mM in DMSO) into blood cell diluent. The tubes were kept at room temperature for 30 minutes. The samples were washed three times and resuspended in blood cell diluent (1 mL).

Analysis was done on a FACS$^R$ 440 dual laser flow cytometer using 488 nm excitation wavelength from an argon ion laser (200 mW) and 633 nm excitation wavelength from a helium-neon laser (45 mW). A bandpass 530/30 emission filter was used for both FDA and BCECF-AM, while a bandpass 660/20 emission filter was used for VBDB. Data from 10,000 events were acquired from each of these samples immediately after staining, one hour after staining, and two hours after staining.

Referring to FIG. 2, VBDB, BCECF-AM and FDA were compared as vital dyes by staining lysed whole blood and examining the fluorescence by flow cytometry. All dyes are membrane permeable esterase substrates which are cleaved by intramolecular esterases to provide a fluorescent dye. Four samples of cells were incubated with BCECF AM (1 uM), FDA (1 uM) and VBDB (0.8 uM, 8.0 uM). The cells were analyzed immediately after staining (t=0), after one hour (t=1) and after two hours (t=2).

Cells stained with FDA did not retain their initial fluorescence over time. Cells stained with VBDB at the lower concentration (0.8 uM) maintained their initial fluorescence; cells stained with both BCECF AM and VBDB at the higher concentration (8 uM) actually increased their fluorescence slightly after one hour. This difference in membrane permeability or "leakiness" of the fluorescent dyes is probably due to the charge of the free dye: the more negatively charged or ionic the dye, the less permeable it is to the cell membrane. Vita Blue and fluorescein both have two ionizable protons; however the sulfonic acid group on Vita Blue has a $pK_a$ which is likely to be several units lower than the carboxylic acid group on fluorescein. Due to the sulfonic acid group, therefore, a greater percentage of Vita Blue than fluorescein is likely to be in the anionic or dianionic form at physiological pH 6-7. BCECF acid contains five ionizable protons (four are carboxylic acids). It shows excellent retention by cells in comparison to other dyes and is useful for comparison.

The data in FIG. 2 also was used to quantitate the "live" cells and the "dead" cells. Two peaks appear in the fluorescence histogram. It was assumed the live cells were those cells which retained the dye (the right peak) and that dead cells were those cells whose membranes had become leaky (the left peak). By setting the gate to the immediate left of the main peak, the "dead" cells to the left of the gate were counted. Over time, in the case of BCECF-AM, the number of dead or dying cells remained virtually constant (t=0, 19%; t=1, 21%; t=2, 21%). For VBDB at the higher concentration (8 uM), the number of dead cells increased (t=0, 12%; t=2, 17%; t=2, 22%). For VBDB at the lower concentration (0.8 uM), the number of dead cells also increased (t=0, 14%, t=1, 18%; t=2, 20%). The number of "leaky" cells for both VBDB and BCECF was greater than the percentage of "dead" cells counted initially using ethidium bromide and acridine orange (3-4%). This difference is probably due to the different permeabilities of the dyes to the cell membrane.

A higher concentration of VBDB than BCECF was required to achieve similar coefficient of variations (CVs) in the fluorescence histogram. For BCECF, the CVs decreased slightly over time: t=0, CV=31%, t=1, CV 28%; t=2, CV 28%. For VBDB, the CVs increased slightly over time. For the lower concentration of VBDB (0.8 uM): t=0, CV=39%; t=1, CV 43%; t=2, CV 46%. For the higher concentration of VBDB (8 uM): t=0, CV=30%; t=1, CV=35%; t=2, CV=34%. The higher concentration of dye did not seem to be deleterious to the cells; the same number of "leaky" cells after two hours were found for both BCECF and VBDB.

Figure 3:
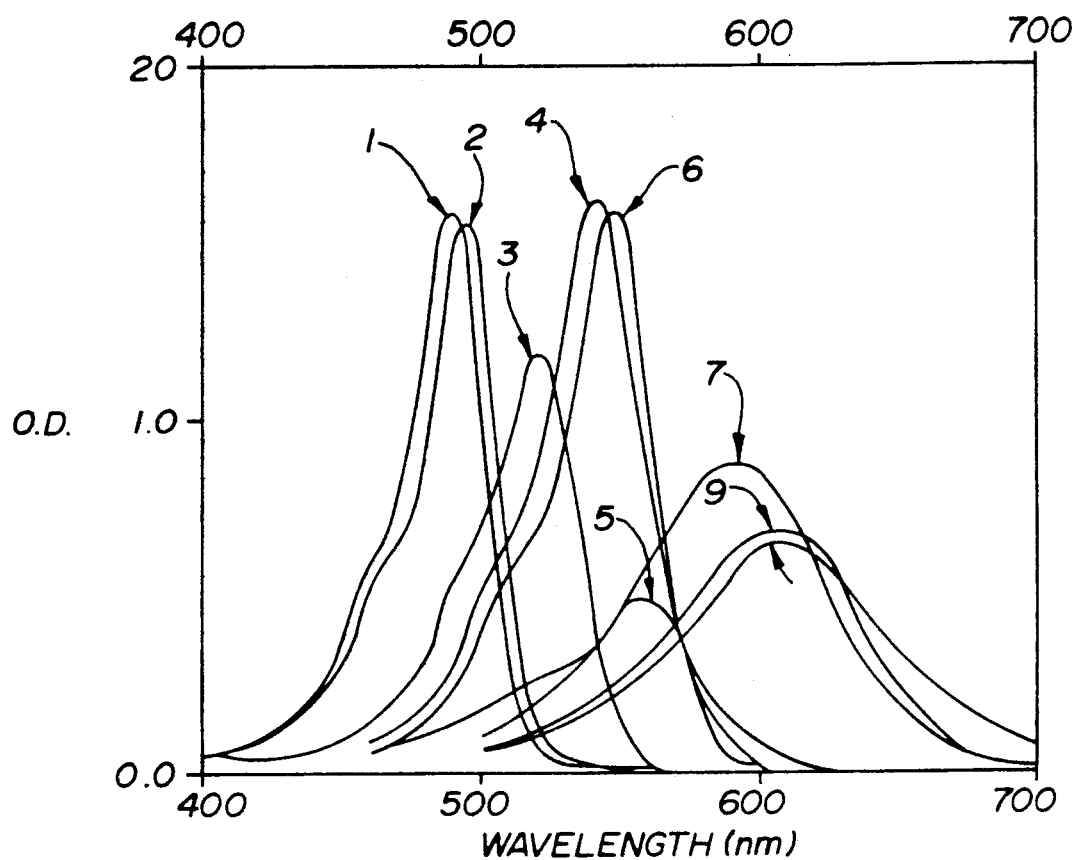
FIG. 3 is a plot of absorbance (O.D.) versus wavelength for compounds 1–9.
Figure 4:
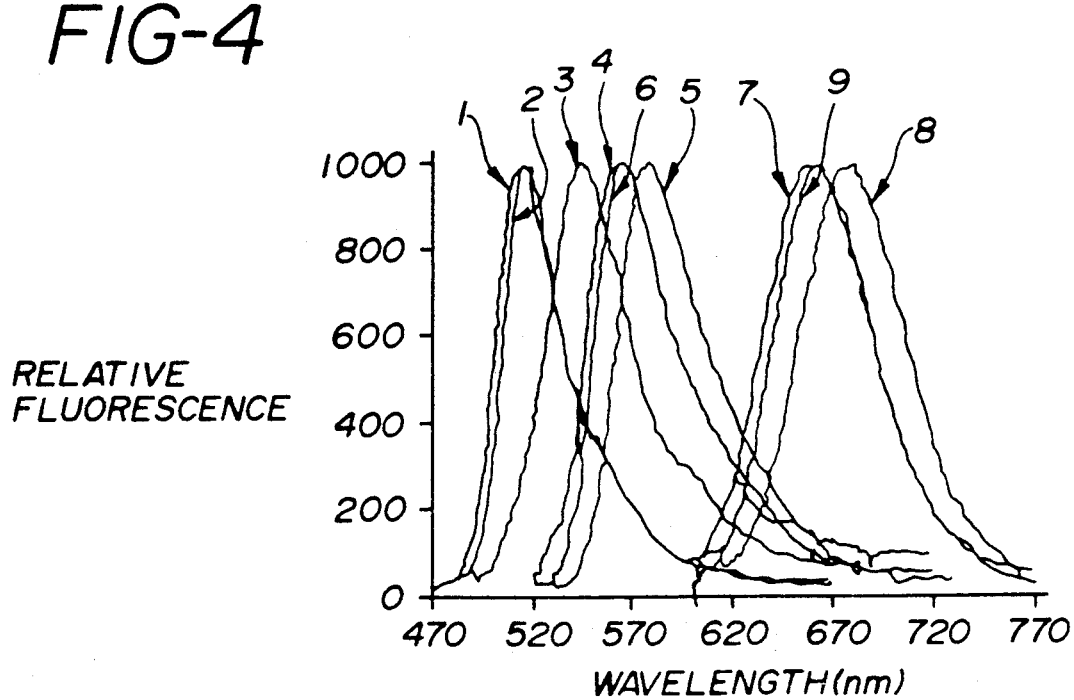
FIG. 4 is a plot of relative fluorescence emission versus wavelength for compounds 1–9.

Finally, the spectral characteristics of compounds 1-9 was determined. The extinction coefficients and quantum yields or compounds 1-9 were determined at pH 9.5. The extinction coefficient and quantum yield of monoprotonated Vita Blue was also determined at pH 5.2. The extinction coefficient and the quantum yield of VBDB were determined at pH 7.2. FIG. 3 shows the absorbance spectra of compounds 1-9; FIG. 4 shows the normalized emission spectra of compounds 1-9.

Figure 5B:
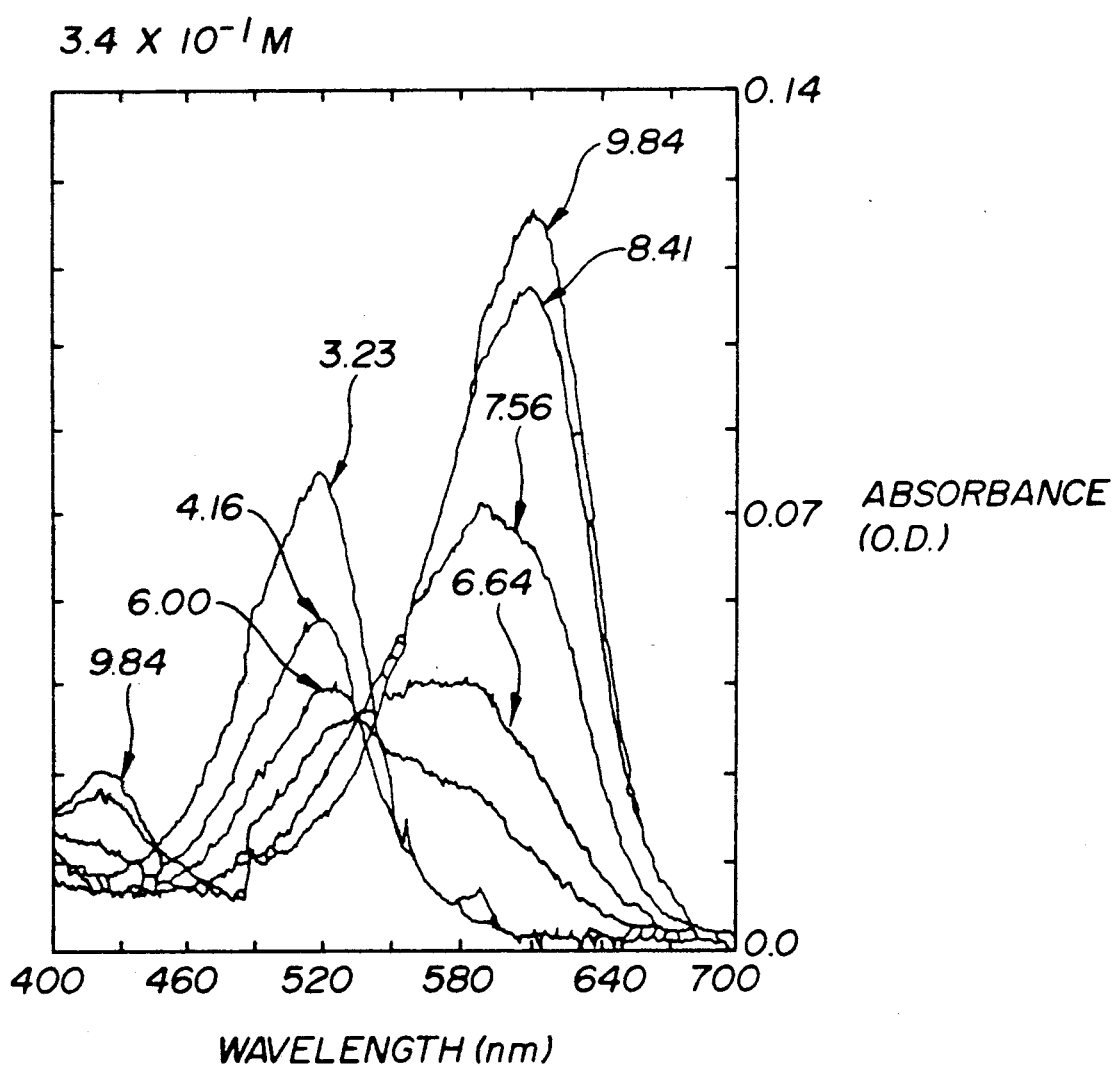
FIG. 5 is a plot of absorbance (O.D.) versus wavelength Blue at a concentration of $1.7 \times 10^{-5}$ M (a) and $3.4 \times 10^{-6}$ M (b) at varying pH.
Figure 6:
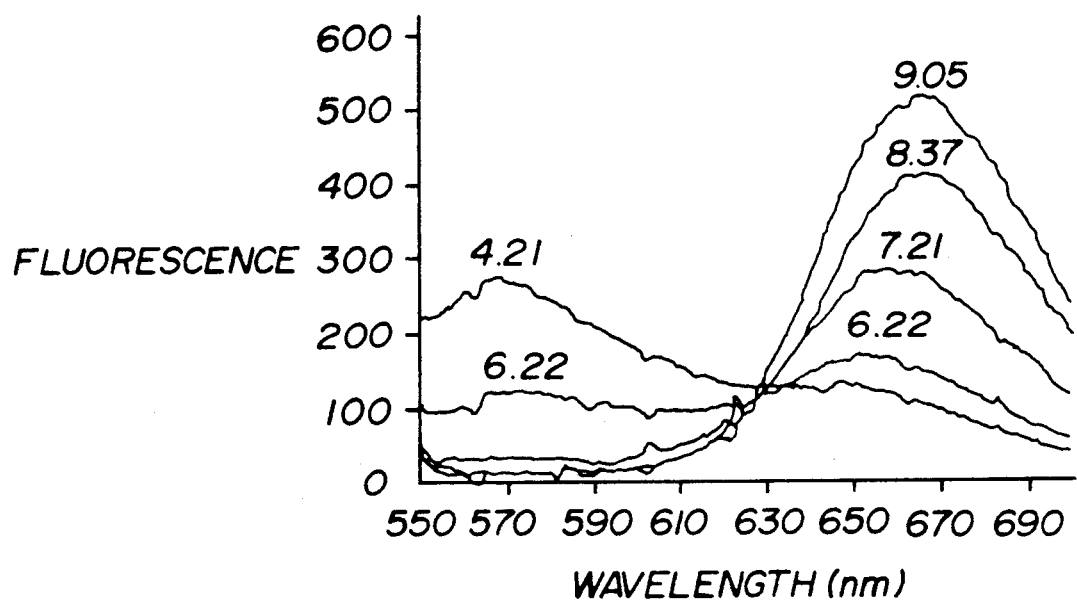
FIG. 6 is a plot of fluorescence versus wavelength for Vita Blue at varying pH.

Compound 9 was unique among the dyes in Table I in that it showed dual fluorescence (i.e., both the mono- and diprotonated forms were fluorescent, but with different excitation and emission maxima). FIG. 5 shows absorbance spectra of Vita Blue at varying pH values at two different concentrations. Apparently, a dimer is formed at the higher concentration; the peak with a maximum at 600 nm in the spectra of 9 ($1.7 \times 10^{-5}$ M, pH 3.10, 4.06 and 6.45) is not visible in the absorbance spectra at the lower concentration ($3.4 \times 10^{-6}$ M). An isobestic point at approximately 540 nm is apparent in the absorbance titration at the lower concentration. FIG. 6 shows emission spectra of compound 9 at varying pH values; the excitation wavelength used was 540 nm. The emission spectra show an isobestic point at 630 nm.

The $pK_{a3}$ values of the dyes were determined by fluorescence titration. The $pK_a$ values shown were determined from absorbance titration. The main difficulty in using absorbance titration or pH titration to determine the $pK_{a3}$ value of fluorescein and related compounds is that it is impossible to make a solution of solely the monoanionic form because the values of $pK_{a2}$ and $pK_{a3}$ differ only by 2.3 units. Since the absorbance spectra of all the different protonated forms overlap, it is difficult to obtain extinction coefficients of the different forms. For the $pK_{a3}$ determination by fluorescence titration, it was assumed that only the dianionic form was fluorescent, and therefore a measurement of fluorescence is directly proportional to the concentration of the dianionic species. In fact, for Vita Blue, both the dianionic and monoanionic forms were fluorescent. However, since the quantum yield of the monoanionic form (0.04) was much lower than the dianionic form (0.15) and the emission maxima of the two forms were separated by 100 nm, the contribution of the monoanionic fluorescence to the analysis was minimal.

A cuvette containing the dye in aqueous, basic solution was titrated with concentrated acid. the pH and fluorescence at one excitation and one emission wavelength were measured. Equation 1 describes the relationship between pH and $pK_{a3}$ for an acid, where $[HA^{1-}]_0$ is the total concentration of the acid (e.g., fluorescein) and $[A^{2-}]$ is the concentration of the acid in the dianionic form. By making the assumption that the fluorescence of the dye is proportional to the concentration of the deprotonated from, equation 1 can be rewritten as equation 2, where $[A^{2-}]/[HA^{1-}]_0$ = normalized fluorescence (nf). The value for the normalized fluorescence factor, or maximum fluorescence, is defined as the fluorescence when $[A^{2-}]=[HA^{1-}]_0$.

$$pH = pK_{a3} - \log\left(\frac{1 - [A^{2-}]/[HA^{1-}]_0}{[A^{2-}]/[HA^{1-}]_0}\right) \quad \text{Eq. 1}$$

-continued $$pH = pK_{a3} - \log\left(\frac{1 - nf}{nf}\right) \quad \text{Eq. 2}$$

Figure 7:
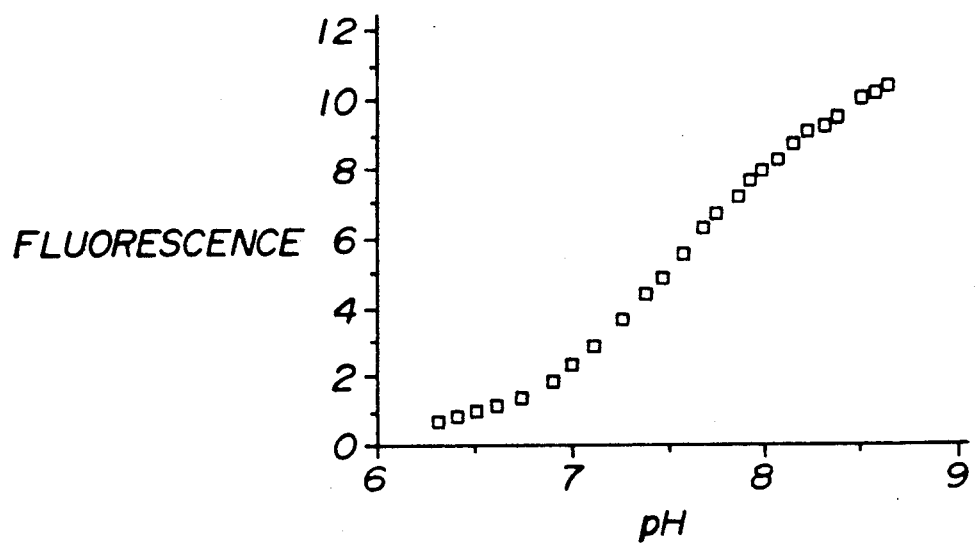
FIG. 7 is a plot of fluorescence versus pH for Vita Blue.
Figure 8:
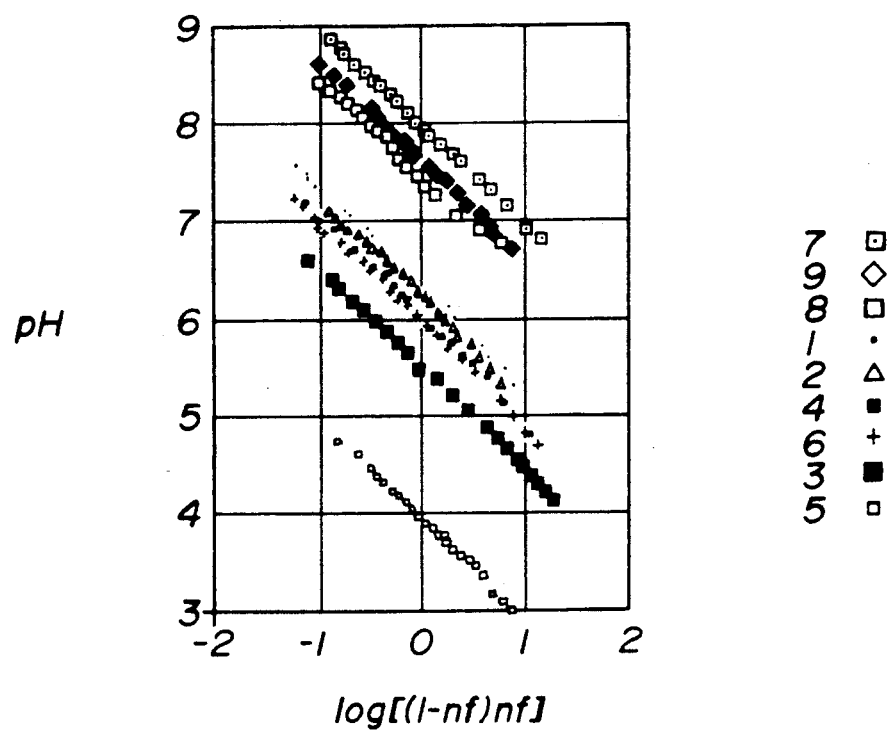
FIG. 8 is a plot of pH versus $\log[(1-nf)/(nf)]$ for the data in Table I, where "nf" is normalized fluorescence.

For example, FIG. 7 shows a plot of pH vs. fluorescence of the data obtained from the fluorescence titration of Vita Blue. The inflection point was estimated to be a pH 7.6. The data at pH 8.6 and above was discarded. FIG. 8 shows a plot of the data of all of the dyes in Table I (log [(1-nf)/nf] vs. pH) using a normalized fluorescence factor which resulted in the slope of the line to be closest to one. a straight line was drawn through the points, and the $pK_{a3}$ was determined to be the value of the pH when the value of log [(1-nf)/nf] was zero. In the case of Vita Blue, the titration was repeated. The two values of the $pK_{a3}$ were 7.54+/−0.03 and 7.57+/−0.03; the average value was 7.56+/−0.03.

An examination of Table I shows that the addition of two bromo groups on compounds 5 and 8 lower the $pK_{a3}$ compared to the parent compounds 4 and 7 as anticipated. The extinction coefficients and quantum yields of compounds 5 and 9 were also lower than the parent dyes, and the excitation maxima were at longer wavelengths, as expected by analogy to fluorescein and eosin. In general, the sulfo group on compounds 2, 6 and 9 shifted both the absorbance maxima (6-14 nm) and the emission maxima (1-5 nm) to the red as compared to the carboxy analogs 1, 4 and 7. The sulfo group on compounds 2 and 6 lowered the $pK_{a3}$ very slightly or not at all as compared to the carboxy analogs, 1 and 4; however, the sulfo group on Vita Blue lowered the $pK_{a3}$ by 0.4 units compared to the carboxy analog, 7. The effect of the sulfo group on compounds 2 and 9 had little effect on the extinction coefficients and the quantum yield as compared to the carboxy analogs, 1 and 7. However, the sulfo analog, compound 6, had twice the quantum yield as the carboxy analog, 4.

Another effect of the sulfo groups on compounds 2, 6 and 9 was to inhibit sulfolactone formation in diacetate synthesis. Compound 2 formed a mixture of the green monoacetate and yellow diacetate in acetic anhydride; the diacetate could be purified by rapid chromatography on silica gel. Compound 6 decomposed before forming the diacetate in refluxing acetic anhydride. Vita Blue also formed a colored diacetate; after refluxing Vita Blue several hours in acetic anhydride the diacetate could be collected as a red solid. The $^1$H NMR spectra of the diacetates of both compounds 2 and 9 showed two acetates per dye; the fact that the diacetates were colored suggested that their structure is an equilibrium between the closed, sulfolactone form and the open, zwitterionic form. The dibutyrate derivative of compound 9 and the diacetate derivative of 2 were relatively stable in water at pH 7. The dibutyrate derivative of compound 9 was fluorescent, as the zwitterionic structure might suggest, with an extinction coefficient of $5.9 \times 10^3$ at 480 nm and a quantum yield of 0.03 (excitation maximum=480 nm, emission maximum=550 nm).

VBDB was found to be a good substrate for pig liver esterase (E.C.3.1 1.1). The Michaelis constant ($K_m$) of VBDB at pH 8.0 was found to be $4 \times 10^{31\ 5}$ M (FIG. 1). This $K_m$ can be compared to that of ethyl butyrate ($4.4 \times 10^{-4}$ M). The fact that the $K_m$ of VBDB is actually lower than that of ethyl butyrate suggests that the large steric bulk of the chromophore does not inhibit enzymatic hydrolysis. Diacetate ester of compounds 2 and 9 were also esterase substrates; however, neither diacetates were membrane permeable.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed:

1. A method for staining cells in a sample which comprises incubating said with a tagging agent which specifically binds to said cells under conditions sufficient to allow said cells to bind with said tagging agent, said tagging agent being coupled to a fluorescent compound selected from the group consisting of

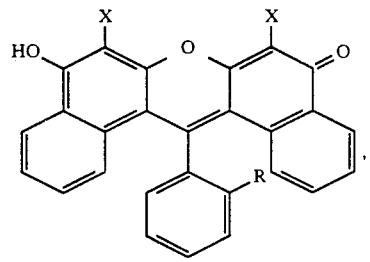

wherein R is $CO_2H$ or $SO_3H$, and X is H or Br when R is $CO_2H$ and X is H when R is $SO_3H$;

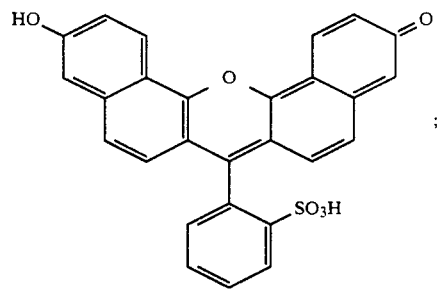

;

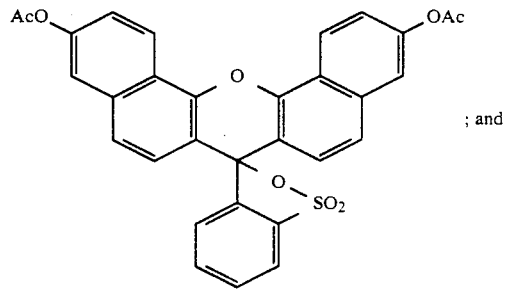

; and

-continued

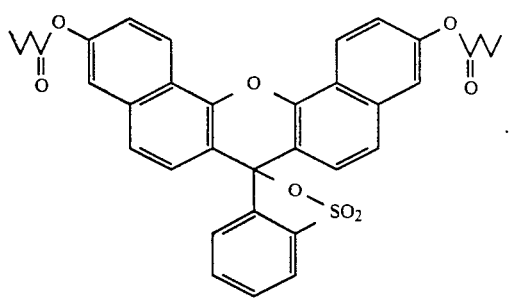

2. The method of claim 1 wherein the tapping agent is in antibody.

3. The method of claim 2 wherein the antibody is a monoclonal antibody.

4. The method of claim 1 wherein the tagging agent is coupled to the compound via a biotin-avidin complex.

5. The method of claim 1 wherein the cells are derived from body tissue or body fluids.

6. The method of claim 1 wherein the compound is

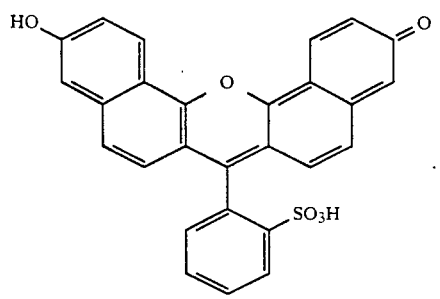

7. The method of claim 1 wherein the compound is

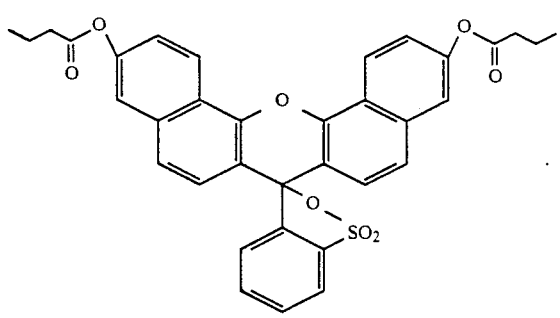

8. A method for identifying cells in a sample which comprises:
(a) incubating said cells with a tagging agent which specifically binds to said cells under conditions sufficient to allow said cells to bind with said tagging agent, said tagging agent being coupled to a fluorescent compound selected from the group consisting of of the formula

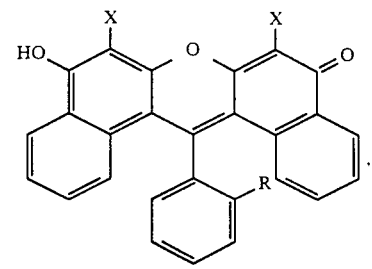

wherein R is $CO_2H$ or $SO_3H$, and X is H or Br when R is $CO_2H$ and X is H when R is $SO_3H$;

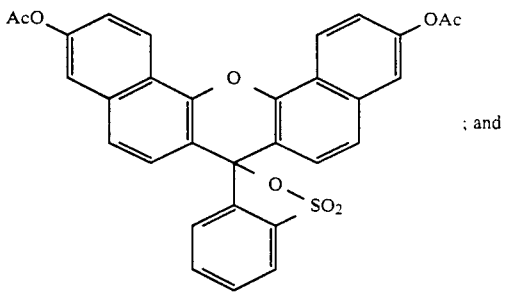
;

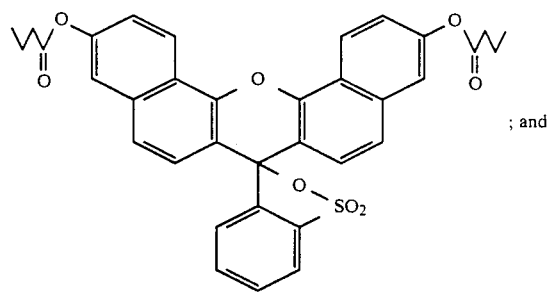
; and

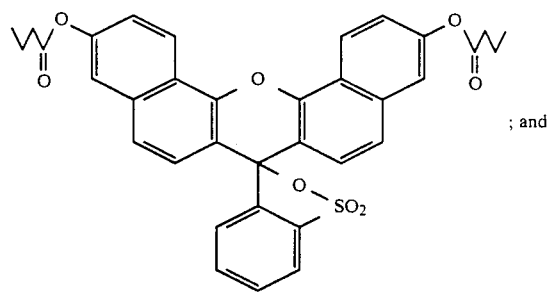
; and (b) detecting fluorescence emitted by said bound tagging agent as a measure of the presence of said cells.

9. The method of claim 8 wherein the tagging agent is an antibody.

10. The method of claim 9 wherein the antibody is a monoclonal antibody.

11. The method of claim 8 in which the tagging agent is coupled to the compound via a biotin-avidin complex.

12. The method of claim 8 wherein the cells are derived from body tissue or body fluids.

13. The method of claim 8 wherein fluorescence is detected using a flow cytometer.

14. The method of claim 8 wherein the compound is

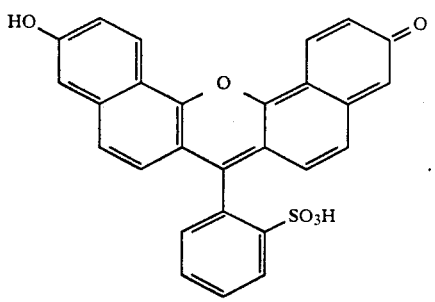

15. The method of claim 8 wherein the compound is

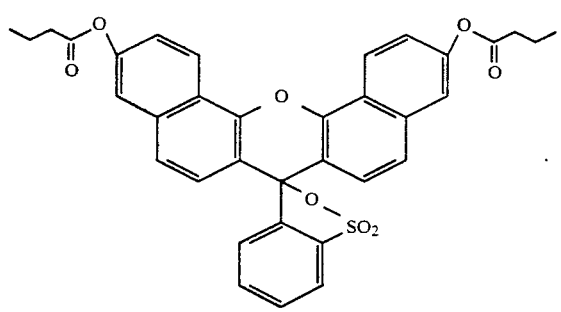

16. A method for discriminating between live cells and dead cells in a sample which comprises:

(a) incubating said cells with a fluorescent compound selected from the group consisting of

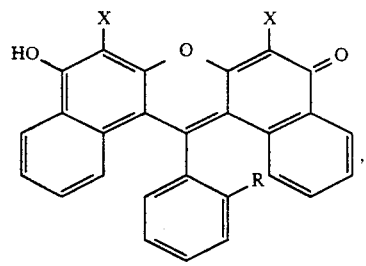

wherein R is $CO_2H$ or $SO_3H$, and X is H or Br when R is $CO_2H$ and X is H when R is $SO_3H$;

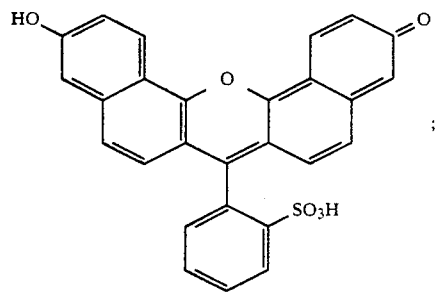

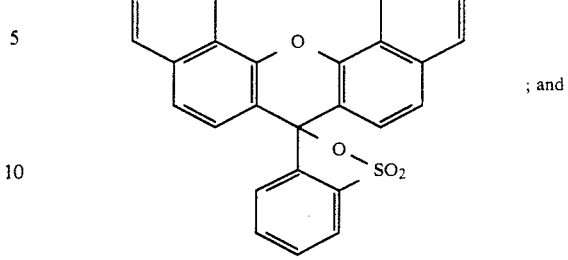

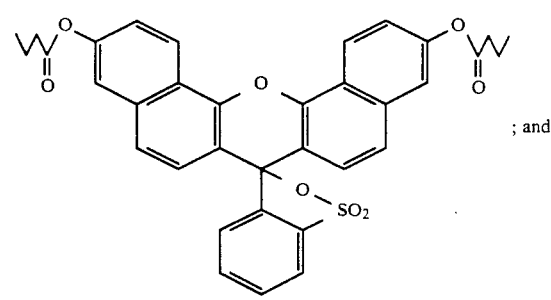

under conditions sufficient to allow uptake of said compound by said live cells; and (b) detecting fluorescence emitted by said compound as a measure of the presence of said live cells.

17. The method of claim 16 wherein the compound is

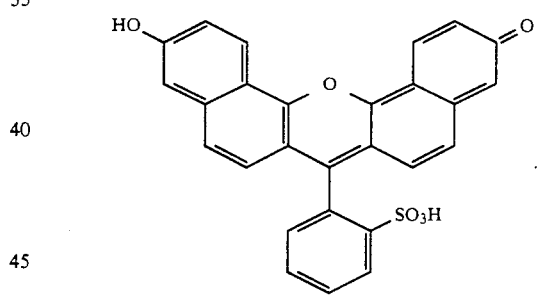

18. The method of claim 16 wherein the compound is

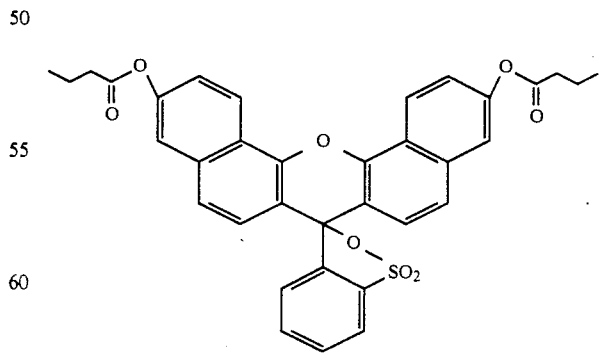

19. A method for detecting an esterase activity in a sample of cells comprising a) incubating said cells with a fluorescent compound selected from the group consisting of

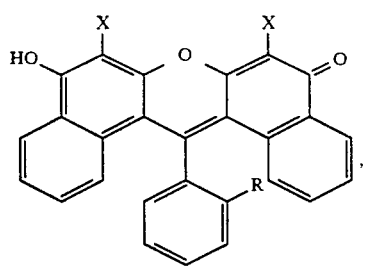

wherein R is CO₂H or SO₃H, and X is H or Br when R is CO₂H and X is H when R is SO₃H;

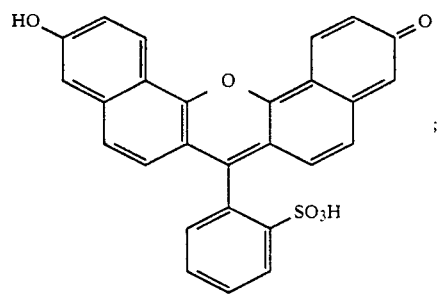

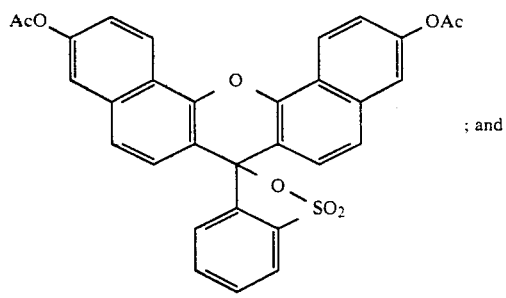

; and

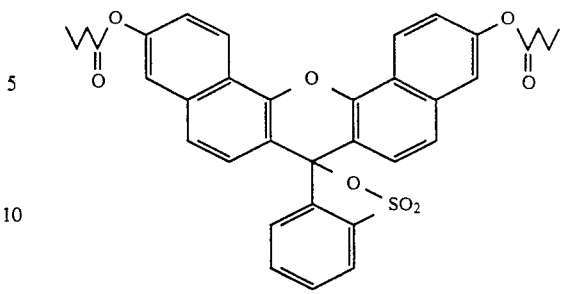

under conditions sufficient to allow uptake of said compound by said cells and cleavage of said compound by said esterase activity b) detecting fluorescence emitted by said cleaved compound as a measure of said esterase activity.

20. The method of claim 19 wherein the compound is

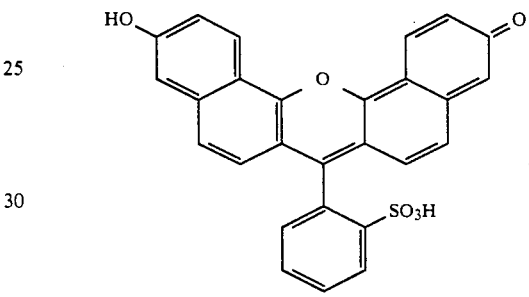

21. The method of claim 19 wherein the compound is

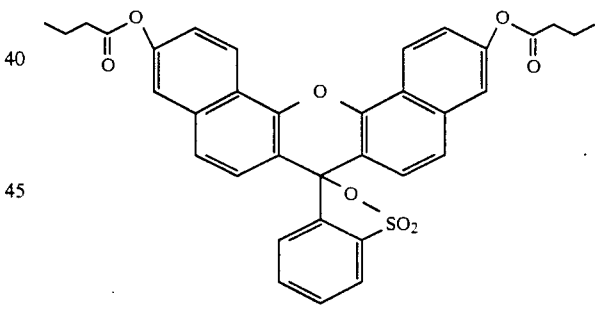

* * * * *